US00PP22693P2

(12) United States Plant Patent
Goodwin

(10) Patent No.: US PP22,693 P2
(45) Date of Patent: May 1, 2012

(54) SWEET CHERRY TREE NAMED 'GOODWIN'

(50) Latin Name: *Prunus avium*
Varietal Denomination: Goodwin

(75) Inventor: Gordon C. Goodwin, Wenatchee, WA (US)

(73) Assignee: Van Well Nursery, Inc., Wenatchee, WA (US)

( * ) Notice: Subject to any disclaimer, the term of this patent is extended or adjusted under 35 U.S.C. 154(b) by 2 days.

(21) Appl. No.: 12/928,046

(22) Filed: Dec. 1, 2010

(51) Int. Cl.
*A01H 5/00* (2006.01)

(52) U.S. Cl. ..... Plt./181

(58) Field of Classification Search ..... Plt./181
See application file for complete search history.

*Primary Examiner* — Susan McCormick Ewoldt
(74) *Attorney, Agent, or Firm* — Michelle Bos

(57) ABSTRACT

'Goodwin' is a new sweet cherry variety notable for its late maturity and large, attractive fruit.

4 Drawing Sheets

Genus and species: *Prunus avium.*
Variety denomination: 'Goodwin'.

CROSS-REFERENCE TO RELATED APPLICATIONS

None.

STATEMENT REGARDING FEDERALLY SPONSORED RESEARCH OR DEVELOPMENT

None.

BACKGROUND AND SUMMARY OF THE VARIETY

The new sweet cherry variety 'Goodwin' is believed to be a whole tree mutation of 'Sumleta' cherry (U.S. Plant Pat. No. 11,378). The inventor planted 'Sumleta' cherry trees in his commercial cherry orchard on Stemilt Hill near Wenatchee, Wash. in 2000. In 2003, he observed that one of the trees was different from the others. In particular, he noted that its fruit matured a week after 'Sumleta' and a full 30 days after 'Bing' (not patented). The mutated tree was asexually propagated by budding onto 'Mazzard' (not patented) rootstock at Quincy, Wash. in 2003. These second generation trees were planted in the orchard in 2005, and fruited in the spring of 2008. In 2005, 150 trees were propagated on 'Gisela 6' (U.S. Plant Pat. No. 8,954) rootstock using scionwood taken from the second generation trees. These third generation trees were planted in the spring of 2007 and fruited in the spring of 2010. All of the trees through the third generation have consistently carried the same late maturing characteristics of the parent tree.

'Goodwin' was initially selected for, and is distinguished by, its late maturing fruit. It has also been observed that the blossoms of 'Goodwin' are hardier than those of 'Sumleta' and 'Bing'. Approximately 12 days after full bloom, representative branches of 'Bing', 'Sweetheart', 'Skeena' (U.S. Plant Pat. No. 11,392), and 'Goodwin' were collected and blossom hardiness was compared. Table 1 illustrates the improved blossom hardiness of 'Goodwin' as compared to the other varieties.

TABLE 1

| Variety | Number of viable fruits per 100 blossoms |
|---|---|
| 'Goodwin' | 95 |
| 'Sweetheart' | 47 |
| 'Skeena' | 46 |
| 'Bing' | 42 |

The following table illustrates additional distinguishing characteristics of 'Goodwin' as compared to 'Sumleta' and 'Bing.'

TABLE 2

| Characteristic | 'Goodwin' | 'Sumleta' | 'Bing' |
|---|---|---|---|
| Maturity date | +30 | +7 | 0 |
| Pollination requirement | Self-fruitful | Self-fruitful | Pollenizer required |
| Productivity | Much heavier than 'Bing' | Heavier than 'Bing' | Standard |
| Fruit Size | Equal to or larger than 'Sumleta' | Larger than 'Bing' | Standard |

BRIEF DESCRIPTION OF THE PHOTOGRAPHS

Figure 1:
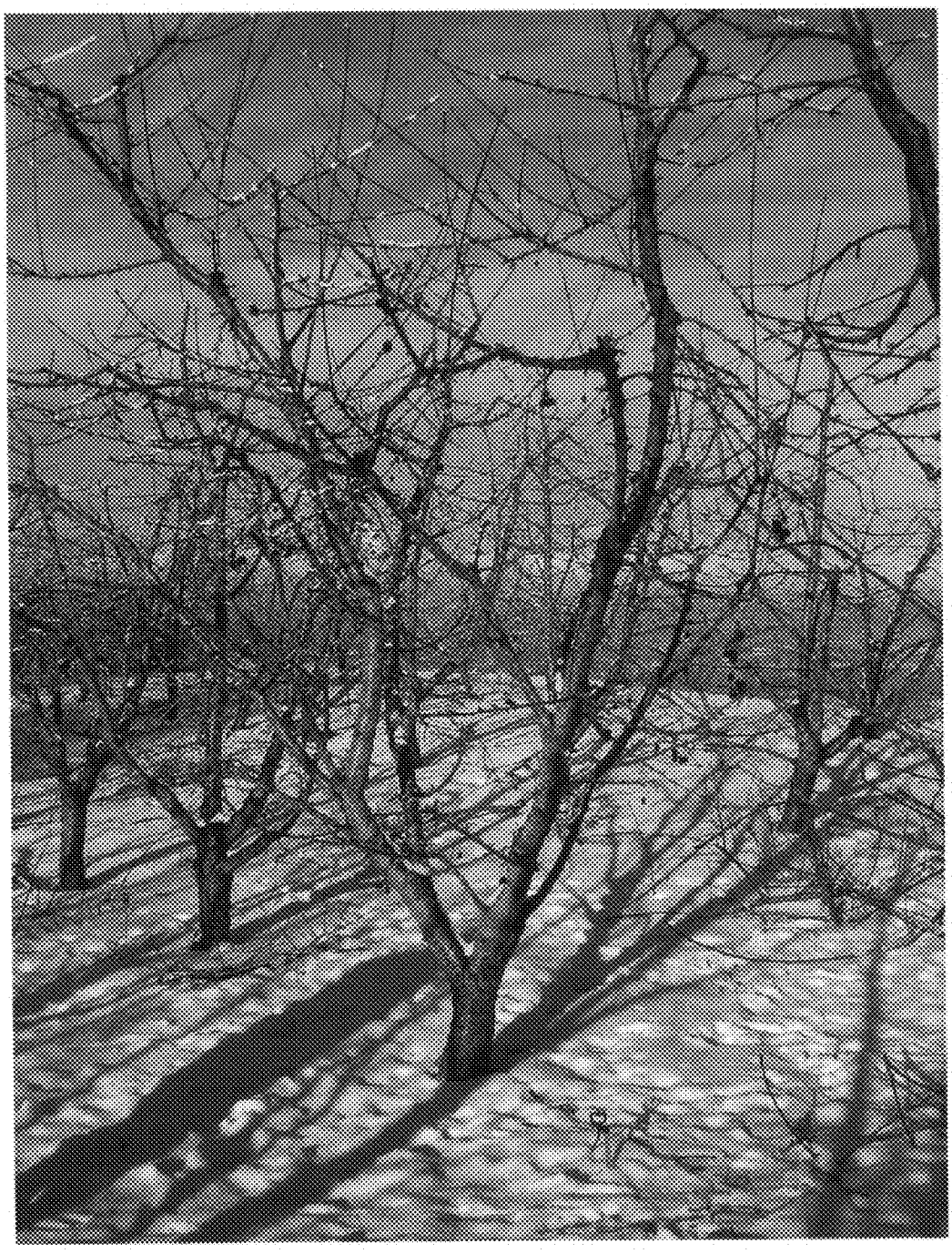
Figure 2:
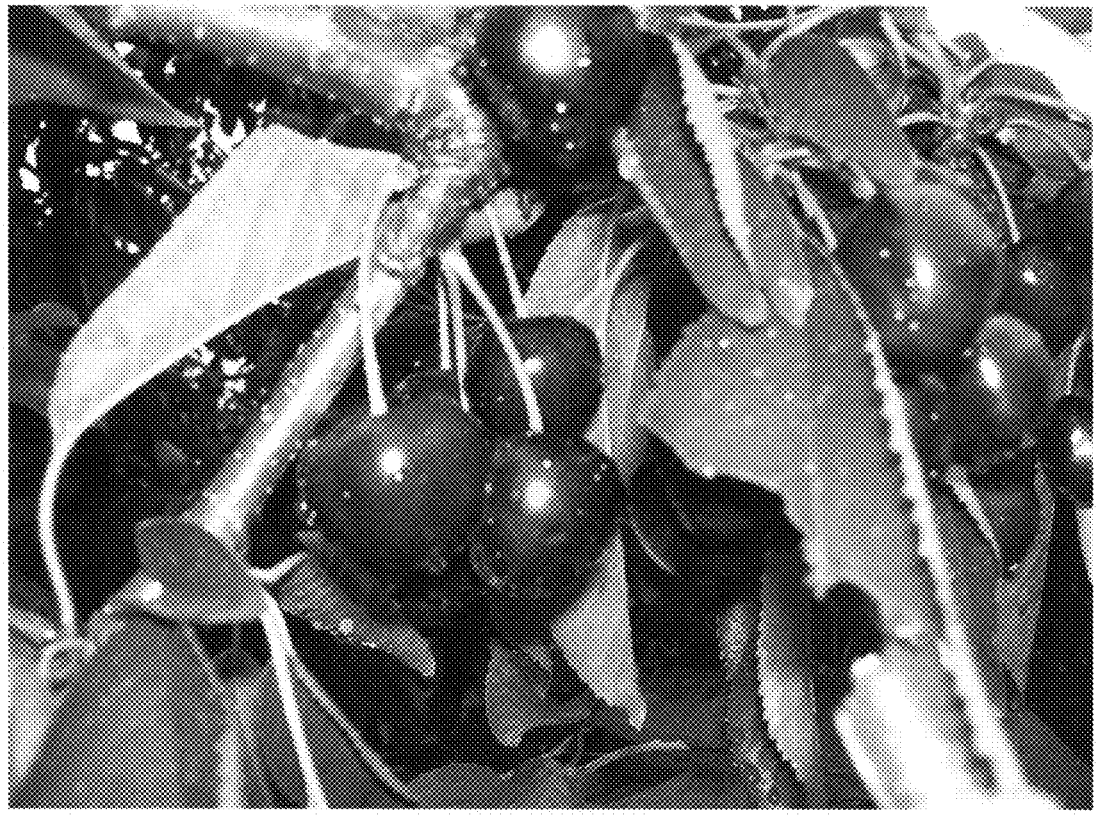
Figure 3:
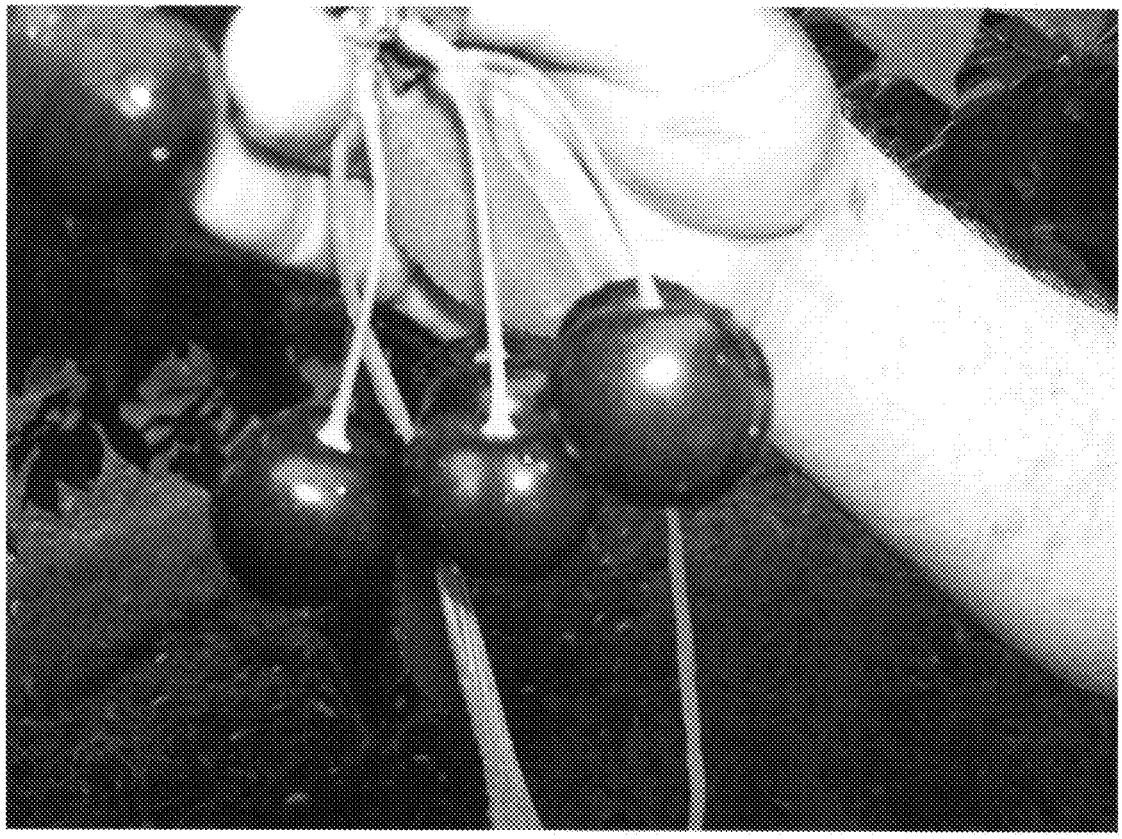
Figure 4:
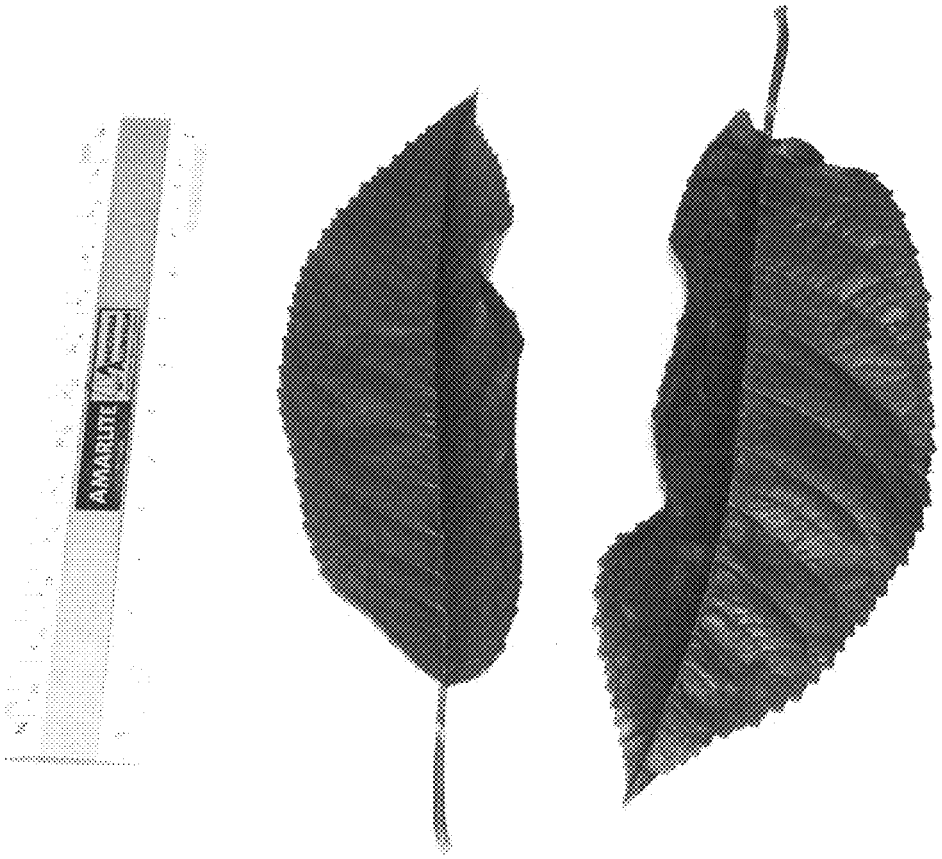

FIG. 1 shows the original tree of the new variety;
FIG. 2 shows a branch of the new variety;
FIG. 3 shows fruit of the new variety; and
FIG. 4 shows leaves of the new variety.

The colors of these illustrations may vary with lighting conditions. Color characteristics of this new variety should therefore be determined with reference to the observations described herein, rather than from the illustrations alone.

DETAILED BOTANICAL DESCRIPTION

The following detailed botanical description is based on observations of the original tree of the variety, planted in 2000 and grown on 'Mazzard' rootstock (not patented). Observations were recorded and photographs taken during the 2009 growing season at Wenatchee, Wash. The characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average. Colors are described with reference to the Munsell Book of Color.

Tree:

*Vigor*.—Highly vigorous.
*Habit, shape*.—Upright, spreading.
*Density*.—Average for sweet cherry trees.
*Height*.—5 m.
*Spread*.—4 m.
*Trunk diameter* (*at 50 cm above the soil line*).—30 cm.
*Bark texture*.—Typical sweet cherry; smooth with vertical striations and horizontal lenticels.
*Bark coloration*.—7.5 R 2/4 (reddish brown), similar to 'Sumleta'.
*Lenticel size*.—Similar to 'Sumleta'.
*Lenticel color*.—Similar to 'Sumleta'.
*Lenticel quantity*.—Similar to 'Sumleta'.

Branch (main structural branches):

*Diameter*.—12 cm at 30 cm from trunk.
*Crotch angle*.—60° to 90°.
*Bark color*.—7.5R 2/4 (reddish brown).
*Bark texture*.—Typical of sweet cherry; smooth with vertical striations and horizontal lenticels.
*Lenticels*.—1 mm×5 mm on 2 year old wood; 3 mm×10 mm on 4 year old wood; color 5YR 8/2 (tan); about 2 per $cm^2$ on young wood, 1 per $cm^2$ on older wood.

One year old shoot:

*Length*.—60 cm.
*Color*.—2.5Y 4/4 (greenish brown).
*Thickness*.—1 cm at base.
*Internode length*.—Similar to 'Sumleta', 10 to 15 cm.
*Pubescence*.—Absent.
*Lenticel size*.—0.5 mm diameter.
*Lenticel color*.—2.5Y 6/4 (light greenish tan).
*Lenticel quantity*.—Approximately 3 per $cm^2$.

Flower buds:

*Quantity per spur*.—1-5, average 3 per node.
*Shape*.—Elongate, conic.
*Length*.—5 mm.
*Diameter*.—2 mm.
*Color*.—Closed bud 5GY 6/8 (green).

Flowers:

*Diameter of fully open flower*.—25 to 30 mm.
*Depth of fully open flower*.—10 to 15 mm.
*Relative position of petal margin*.—Slightly overlapping.
*Pedicel length*.—Medium, 20 to 30 mm, shorter than 'Bing', similar to 'Brown' (U.S. Plant Pat. No. 15,386).
*Pedicel diameter*.—1 mm.
*Pedicel color*.—7.5GY 7/8 (light green).
*Number of flowers per cluster*.—5 to 8.
*Date of first bloom*.—Apr. 20, 2009 (Stemilt Hill, Wenatchee).
*Date of full bloom*.—Apr. 22, 2009 (same as 'Bing').
*Pollination requirement*.—Self fertile.

Petals:

*Number per flower*.—5.
*Length*.—15 to 17 mm.
*Width*.—13 mm.
*Petal shape*.—Abovate, cupped slightly inward.
*Apex shape*.—Round.
*Base shape*.—Acute.
*Margin*.—Typical of sweet cherry.
*Coloration of upper surface*.—White.
*Coloration of lower surface*.—White.

Pistil:

*Size*.—Length 12 mm, diameter 1 mm.
*Color*.—5GY 9/2 (pale yellowish green).

Stigma:

*Size*.—1 mm diameter.
*Color*.—2.5Y 7/6 (buff).

Style:

*Size*.—17 mm from ovary to stigma.
*Color*.—10Y 9/4 to 2.5Y 7/6 (pale yellow to buff).

Ovary (unfertilized):

*Size*.—2 mm×4 mm.
*Color*.—5GY 6/8 (green).

Stamens:

*Quantity*.—20 to 30.
*Anther size*.—Medium, 0.5 mm.
*Anther color*.—5Y 8.5/4 (yellow).
*Filament size*.—10 to 15 mm.
*Filament color*.—Similar to 'Bing'.
*Presence/abundance of pollen*.—Abundant.
*Color of pollen*.—5Y 8.5/4 (yellow).

Sepals:

*Quantity*.—5.
*Color*.—5GY 7/4 (light green).
*Shape*.—Elongated, recurved (similar to 'Bing').
*Apex*.—Acute.
*Base*.—3 to 4 mm in width.
*Margin*.—Smooth, with fine pubescence.
*Length*.—6-8 mm.
*Width*.—3-4 mm.

Leaves:

*Length*.—12.5 cm.
*Width*.—5.8 cm.
*Blade margin*.—Irregularly serrate to occasionally crenate.
*Leaf shape*.—Lanceolate.
*Apex shape*.—Acuminate.
*Base shape*.—Oblate.
*Texture*.—Smooth, with slight depression along veins.
*Attitude in relation to shoot*.—60° to 90° when mature.
*Color of upper surface*.—2.5GY 3/4 (dark green).
*Color of lower surface*.—5GY 4/4 (medium green).

Petiole:

*Length*.—3.0 to 3.5 cm.
*Diameter*.—2.0 to 3.0 mm.
*Coloration*.—10Y 4/2 (olive green).
*Glands*.—2 present, reniform, 7.5Y 6/8 (yellow green) to 7.5R 4/8 (reddish), positioned on rim of petiole groove about 3 cm from base of leaf petiole and about 2 mm below leaf blade.

Fruit:

*Quantity per cluster*.—2 to 4.
*Diameter*.—25 to 30 mm.
*Length*.—25 mm.
*Weight*.—15 to 25 gm.
*General shape in profile*.—Uniform, symmetrical, mostly round, similar in shape to 'Bing' and 'Sumleta'.
*Shape of stem end*.—Flat.
*Shape of apex*.—Rounded, pistil point not indented.
*Diameter of stalk cavity*.—5 to 8 mm.

*Depth of stalk cavity*.—Medium, 2 mm.
*Depth of suture*.—No apparent suture.

Skin:
*Thickness*.—Thin, similar to 'Sumleta'.
*Texture*.—Crisp, similar to 'Sumleta'.
*Color*.—2.5RP 2/2 (red purple); Similar to 'Sumleta' and 'Bing' at equivalent stage of maturity.
*Overcolor*.—Same as ground color.
*Taste*.—Sweet, low acid, similar to 'Sumleta', lower acidity than 'Bing' (thus milder flavor).
*Lenticels*.—Obscure, similar to 'Sumleta'.

Stalk:
*Length*.—3.5 to 4 cm.
*Diameter*.—1 to 2 mm.
*Color*.—5GY 6/4 (green).

Flesh:
*Firmness of flesh*.—Medium firm.
*Flesh texture*.—Crisp, juicy, similar to 'Sumleta'.
*Fibers*.—Not noticeable.
*Aroma*.—None detected.
*Juiciness*.—Very juicy.
*Brix*.—20 to 24 at maturity.
*Flesh color*.—2.5RP 2/2 (deep purple).
*Juice color*.—2.5RP 2/2 (deep purple).

Stone:
*Length*.—10 mm.
*Diameter*.—8 mm.
*Shape*.—Oval, rounded.
*Color*.—10YR 6/4 (light brown).
*Surface texture*.—Smooth.
*Tendency to split*.—None noted.
*Ventral edge*.—Smooth, no wings or ridges.
*Dorsal edge*.—Smooth, with slight ridge from base to apex.

Harvest:
*Time for harvest*.—30 days after 'Bing'; 7 days after 'Sumleta'.
*Number of picks*.—1.
*Amount of fruit produced per tree per harvest*.—Extremely productive, superior to both 'Bing' and 'Sumleta' based on original tree versus adjacent trees; comparison of second and third generation trees not available.
*Bearing* (*annual, biannual*).—Annual.
*Chilling requirement*.—Unknown.
*Cold hardiness*.—Hardy in area tested (North Central Washington, USDA Zone 5).

Disease resistance/susceptibility: None noted.
*Market use*.—Fresh.
*Keeping quality*.—Good.
*Shipping quality*.—Good.

What is claimed is:

1. A new and distinct variety of cherry tree, substantially as illustrated and described herein.

* * * * *